United States Patent [19]

Massey et al.

[11] Patent Number: 4,764,592
[45] Date of Patent: Aug. 16, 1988

[54] CRYSTALLINE HUMAN PROINSULIN AND PROCESS FOR ITS PRODUCTION

[75] Inventors: Eddie H. Massey; Richard L. Jackson, both of Indianapolis, Ind.

[73] Assignee: Eli Lilly and Company, Indianapolis, Ind.

[21] Appl. No.: 41,498

[22] Filed: Apr. 23, 1987

[51] Int. Cl.$^4$ .................... C07K 7/42; C07K 7/40
[52] U.S. Cl. ............................ 530/305; 530/303; 530/304
[58] Field of Search ............... 514/3, 4; 530/303, 304, 530/305

[56] References Cited

U.S. PATENT DOCUMENTS

| | | | |
|---|---|---|---|
| 2,143,590 | 1/1939 | Scott | 530/305 X |
| 2,174,862 | 10/1939 | Sahyun | 530/304 |
| 2,626,228 | 1/1953 | Petersen | 530/304 X |
| 2,663,666 | 12/1953 | Homan | 530/305 |
| 2,836,542 | 5/1958 | Petersen et al. | 530/304 X |
| 2,920,014 | 1/1960 | Petersen et al. | 530/304 |
| 3,102,077 | 8/1963 | Christensen | 530/304 |
| 4,430,266 | 2/1984 | Frank | 530/303 |
| 4,608,364 | 8/1986 | Grau | 514/3 X |
| 4,616,078 | 10/1986 | DiMarchi | 530/305 |
| 4,654,324 | 3/1987 | Chance et al. | 514/3 X |
| 4,701,440 | 10/1987 | Grau | 514/3 |

FOREIGN PATENT DOCUMENTS

| | | | |
|---|---|---|---|
| 0132863 | 11/1978 | Fed. Rep. of Germany | 514/3 |
| 786635 | 11/1957 | United Kingdom | 514/3 |

OTHER PUBLICATIONS

Fullerton, W. W., Potter, R., and Low, B. W., *Proc. Nat'l Acad. Sci.*, 66, 1213–1219 (1970).

*Primary Examiner*—Howard E. Schain
*Attorney, Agent, or Firm*—William C. Martens; Leroy Whitaker

[57] ABSTRACT

This disclosure provides a crystalline human proinsulin, the preparation of which comprises (a) preparing an aqueous mixture containing from about 5 to about 50 mg/ml human proinsulin, from about 0.1 to about 5 mg/ml of a phenolic substance, from about 0.03 to about 0.6 milliequivalents/ml of a salt of a cation selected from the group consisting of lithium, calcium, sodium, potassium, ammonium, magnesium, and barium, and from about 0.2 to about 5 milliequivalents of $Zn^{+2}$ cation;

(b) adjusting the aqueous mixture to a pH in the range of from about 5.4 to about 6.5;

(c) allowing crystal formation to occur; and (d) recovering crystalline human proinsulin from the aqueous mixture.

15 Claims, No Drawings

CRYSTALLINE HUMAN PROINSULIN AND PROCESS FOR ITS PRODUCTION

BACKGROUND OF THE INVENTION

The advent of recombinant DNA methodology has afforded the opportunity to produce any of a wide range of peptides and proteins. One such protein is human proinsulin. Human proinsulin is useful both as an intermediate in the production of human insulin and as a pharmaceutical agent in its own right in the management of diabetes.

In the recombinant DNA production of human proinsulin, the product customarily is handled in an aqueous solution and is freeze-dried to a non-crystalline powder. A crystalline form of human proinsulin, if available, would afford many advantages in terms of, among others, its storability, formulation strategies, and processes for its isolation and purification.

It is to a novel crystalline form of human proinsulin and to a process for its production that this invention is directed.

SUMMARY OF THE INVENTION

Thus, this invention is directed to a crystalline human proinsulin which comprises a salt of a complex of human proinsulin and divalent zinc ion, the cation of said salt being selected from the group consisting of lithium, calcium, sodium, potassium, ammonium, magnesium, and barium.

This invention also is directed to a process for producing the aforedescribed salt, which comprises (a) preparing an aqueous mixture containing from about 5 to about 50 mg/ml human proinsulin, from about 0.1 to about 5 mg/ml of a phenolic substance, from about 0.03 to about 0.6 milliequivalents/ml of a salt of a cation selected from the group consisting of lithium, calcium, sodium, potassium, ammonium, magnesium, and barium, and from about 0.2 to about 5 milliequivalents of $Zn^{+2}$ cation;

(b) adjusting the aqueous mixture to a pH in the range of from about 5.4 to about 6.5;

(c) allowing crystal formation to occur; and (d) recovering crystalline human proinsulin from the aqueous mixture.

DETAILED DESCRIPTION OF THE INVENTION

As noted, this invention is directed to crystalline human proinsulin and to a process for its production.

The crystalline human proinsulin of this invention comprises a salt of a complex of human proinsulin and divalent zinc ion. The complex generally is represented by a hexameric form of human proinsulin by which six molecules of human proinsulin are coordinately bound to two $Zn^{+2}$ ions. The cation is monovalent or divalent and may be any of the following: lithium, calcium, sodium, potassium, ammonium, magnesium, or barium. Preferably, the cation is calcium, sodium, potassium, ammonium, or magnesium, and, more preferably, is sodium, calcium, or ammonium. Most preferably, the cation is calcium or sodium.

In producing the crystalline human proinsulin of this invention, a number of parameters and conditions are important. These are: concentration of human proinsulin; presence and concentration of a phenolic substance; presence, amount, and identity of the cation; presence and amount of zinc ion; and pH.

The human proinsulin concentration for the aqueous medium generally will range from about 5 mg/ml to about 50 mg/ml. The concentration preferably is in a range represented by the lower one-half of the foregoing range. Increasingly preferred ranges are from about 5 mg/ml to about 25 mg/ml; from about 10 mg/ml to about 20 mg/ml; and from about 13 mg/ml to about 17 mg/ml. Optimally, the process is conducted using a human proinsulin concentration of about 15 mg/ml.

The process of this invention employs a phenolic substance. Any of the commonly-available phenols may be employed. Illustrative of such phenols are phenol itself, o-cresol, m-cresol, p-cresol, resorcinol, methyl p-hydroxybenzoate, catechol, and the like. Preferably, the phenolic substance is phenol or a cresol. The phenolic substance is incorporated into the aqueous crystallization mixture in an amount ranging from about 0.1 to about 5 mg/ml. Preferably, the phenolic substance is present in an amount ranging from about 1 to about 3 mg/ml.

The cation of the crystalline human proinsulin is any of the aforedescribed cations. It is added to the aqueous mixture in the form of any of a wide range of salts. Preferably, however, the salt that is used is the chloride salt. It is preferred to avoid use of a bicarbonate salt since, for some reason, the bicarbonate anion appears to inhibit crystallization of the human proinsulin salt. The selected cation is added to the aqueous medium in an amount on a mole:mole basis of from about 10:1 to about 1500:1 cation:human proinsulin. Of course, when the cation is divalent ($Ca^{++}$, $Mg^{++}$, $Ba^{++}$), a lesser amount of the cation customarily will be employed than when the cation is monovalent ($Na^+$, $K^+$, $Li^+$, $NH_4^+$). Typically, when the cation is divalent, it will be present in the mixture at a ratio of about 50:1 relative to human proinsulin and, when monovalent, at a ratio of about 200:1.

In general, when the human proinsulin concentration is about 13 mg/ml or less, crystallization will be retarded by an excessively high cation concentration.

A soluble zinc salt is used in the formation of the crystalline human proinsulin of this invention. Typical such soluble salts are zinc chloride, zinc acetate, zinc nitrate, and the like. The stoichiometric quantity of zinc ion necessary for the crystalline form of human proinsulin in accordance with this invention is one zinc atom per each three human proinsulin molecules. In accordance with the process of this invention, a lesser amount of zinc ion can be employed; however, although crystallization will occur, the yield, of course, will be proportionately reduced.

Generally, therefore, the zinc salt will be used in an amount representing at least the stoichiometric amount (1 $Zn^{++}$/3 HPI) and may range up to a molar ratio of about 2 $Zn^{++}$ per each human proinsulin molecule. Optimally, the crystallization process will be carried out at a $Zn^{++}$ concentration representing about 1 $Zn^{++}$ per every 2 human proinsulin molecules.

For the sake of convenience, the aqueous mixture containing the desired amounts of human proinsulin, phenolic substance, cation, and $Zn^{+2}$ ion is prepared at a pH below about 3.5 or preferably above about 6.5.

The completed mixture, once formed, is pH-adjusted to obtain a pH in the range of from about 5.4 to about 6.5. Preferably, the pH is maintained within the range of about 5.8 to about 6.3, and, most preferably, about 6.0 to about 6.1.

Crystals then are allowed to form from the mixture maintained at a temperature in the range of from about 0° C. to about 40° C. As might be expected, it is preferred to carry out the crystallization at a temperature at the lower end of the foregoing range, for example, from about 5° C. to about 25° C. Moreover, crystallization can be hastened by agitating the mixture, first at about 25° C. and then at about 5° C.

It has been discovered that crystal recovery is greatly enhanced by decanting the mother liquor from the initial crystallization mixture and then washing the crystals with a mother liquor wash. By the term "mother liquor wash" is meant a prepared solution containing the phenolic substance, the salt providing the desired cation, and the zinc salt, each at a concentration approximating that represented in the crystallization mixture.

A further enhancement for recovery of the human proinsulin crystals involves adding a thick slurry of the crystals in the mother liquor wash to at least about 10 volumes of absolute ethanol. This procedure facilitates retention of the human proinsulin in crystalline form.

A general and preferred method for producing the human proinsulin crystals of this invention is as follows:

The human proinsulin is dissolved in water at a concentration of about 15 mg/ml, pH about 6.5 to about 7.0. Phenol or cresol (about 0.3%; 3 mg/ml) is added to the mixture followed by enough cationic salt to make the solution equivalent to about 0.35M for the monovalent salt (NaCl, KCl, LiCl, or $NH_4Cl$) or about 0.077M for the divalent salt ($CaCl_2.2H_2O$, $MgCl_2$, or $BaCl_2$). The pH of the resulting solution is adjusted to about 6.5 after which about 1.16 mM of $ZnCl_2$ (0.8 ml of 2% $ZnCl_2$/100 ml) is added. The pH of the resulting mixture is adjusted to about 6.0-6.1 by addition, as necessary, of dilute NaOH or dilute HCl. The mixture then is agitated for about 24 hours at about 25° C. and then for about 24 hours at about 5° C. The resulting crystals are allowed to settle, and the mother liquor is decanted. The mixture then is centrifuged for about 2-3 minutes at about 2500 rpm, and additional mother liquor is decanted. The crystals are slurried in 1-2 volumes of mother liquor wash, and the mixture is again centrifuged and the liquor decanted. The crystals are once again slurried in 1-2 volumes of mother liquor wash after which the mixture is slowly poured with continuous agitation into 10-15 volumes of absolute ethanol. Agitation is continued for 10-15 minutes after which, upon settling of the crystals, the alcohol wash is decanted. The mixture is centrifuged, decanted, again washed with absolute ethanol, and again centrifuged and decanted. The recovered crystals then are dried in vacuo for about 12-24 hours.

The following example is provided to illustrate production of crystalline human proinsulin in accordance with this invention using a variety of cations. The example is not intended to be limiting upon the broad scope of this invention.

EXAMPLE

Twenty two grams of lyophilized purified human proinsulin were dissolved in 1000 ml purified water to provide a human proinsulin concentration of 19.53 mg/ml. After the addition of 2 ml of liquefied phenol, the solution was diluted to 15.62 mg human proinsulin/ml with 250 ml of 0.2% phenol. The pH of the solution was 6.5. Aliquots of 20 ml each (312.5 mg human proinsulin) were taken, and chloride salts were added as follows: 77 mM $CaCl_2$ (0.456 ml 50% $CaCl_2$ solution); 75, 150, and 300 mM NaCl (87.2, 175.2, and 350.4 mg); 75, 150, and 300 mM KCl (112, 224, and 448 mg); and 75, 150, and 300 mM $NH_4Cl$ (80, 160, and 320 mg). Each was treated with 0.16 ml 2% $ZnCl_2$ (76 μg $Zn^{++}$/ml or 1.16 mM), and the pH was adjusted to 6.0-6.1 with 10% HCl. The mixture was agitated 24 hours at 25° C. and then 24 hours at 5° C. and allowed to settle. Samples of the crystallization mixtures were taken after 24 and 48 hours, filtered, and assayed for human proinsulin to determine the extent of crystallization. The clear supernatant liquid was decanted, and a slurry of the human proinsulin crystals was poured slowly into 10-15 volumes of cold absolute ethanol while agitating rapidly. After stirring for 10-15 minutes, the crystals were centrifuged briefly, the alcohol decanted, and the crystals washed again with alcohol, centrifuged, and the alcohol decanted. The crystals were dried in vacuo and weighed. The Table following, displays the results which were obtained.

TABLE

| Salt | Concentration, M | Crystalline Human Proinsulin Mother Liquor, % HPI | | Dry Crystals | |
|---|---|---|---|---|---|
| | | After 24 hours Room Temperature | After 24 hours 5° C. | mg | % yield |
| $CaCl_2$ | 0.077 | 5.9 | 2.2 | 278 | 89 |
| NaCl | 0.075 | 23.9 | 10.1 | 250 | 80 |
| NaCl | 0.150 | 9.6 | 5.2 | 277 | 89 |
| NaCl | 0.300 | 13.7 | 10.9 | 281 | 90 |
| KCl | 0.075 | 17.8 | 7.8 | 269 | 86 |
| KCl | 0.150 | 9.6 | 5.6 | 282 | 90 |
| KCl | 0.300 | 8.9 | 6.3 | 256 | 82 |
| $NH_4Cl$ | 0.075 | 6.9 | 5.8 | 269 | 86 |
| $NH_4Cl$ | 0.150 | 7.8 | 5.3 | 265 | 85 |
| $Nh_4Cl$ | 0.300 | 9.9 | 6.1 | 269 | 86 |

We claim:

1. A process for producing crystalline human proinsulin, which comprises
   (a) preparing an aqueous mixture containing from about 5 to about 50 mg/ml human proinsulin, from about 0.1 to about 5 mg/ml of a phenolic substance, from about 0.03 to about 0.6 milliequivalents/ml of a salt of a cation selected from the group consisting of lithium, calcium, sodium, potassium, ammonium, magnesium, and barium, and from about 0.2 to about 5 milliequivalents of $Zn^{+2}$ cation;
   (b) adjusting the aqueous mixture to a pH in the range of from about 5.4 to about 6.5;
   (c) allowing crystal formation to occur; and
   (d) recovering crystalline human proinsulin from the mixture.

2. Process of claim 1, in which the concentration of human proinsulin is from about 5 to about 25 mg/ml.

3. Process of claim 2, in which the concentration of human proinsulin is from about 13 to about 17 mg/ml.

4. Process of claim 1, in which the phenolic substance is phenol or a cresol.

5. Process of claim 4, in which the phenolic substance is present in an amount ranging from about 1 to 3 mg/ml.

6. Process of claim 1, in which the salt is a chloride salt.

7. Process of claim 6, in which the cation of the salt is selected from the group consisting of sodium, calcium, and ammonium.

8. Process of claim 7, in which the cation of the salt is sodium.

9. Process of claim 7, in which the cation of the salt is calcium.

10. Process of claim 1, in which $Zn^{+2}$ ion is added in an amount representing from about one $Zn^{+2}$ per each three proinsulin molecules to about two $Zn^{+2}$ per each proinsulin molecule.

11. Process of claim 1, in which the aqueous mixture containing human proinsulin, phenolic substance, cation, and $Zn^{+2}$ is prepared at a pH below about 3.5 or above about 6.5.

12. Process of claim 1, in which the aqueous mixture containing human proinsulin, phenolic substance, cation, and $Zn^{+2}$, once prepared, is brought to and maintained at a pH of from 5.8 to about 6.3.

13. Process of claim 12, in which the final pH is from about 6.0 to about 6.1.

14. Process of claim 1, in which, prior to recovery of the formed crystalline human proinsulin from the aqueous mixture, the mother liquor supernatant is decanted from the mixture, and the residual crystals are washed with a mother liquor wash.

15. Process of claim 14, in which the mother liquor wash containing crystalline human proinsulin is added to at least about 10 volumes of absolute ethanol.

* * * * *

UNITED STATES PATENT AND TRADEMARK OFFICE
CERTIFICATE OF CORRECTION

PATENT NO. : 4,764,592

DATED : August 16, 1988

INVENTOR(S) : Eddie H. Massey and Richard L. Jackson

It is certified that error appears in the above-identified patent and that said Letters Patent is hereby corrected as shown below:

Column 4, line 54, "mixture" should read --aqueous mixture--; line 62, "about 1 to 3" should read --about 1 to about 3--.

Column 6, line 2, "from 5.8 to about 6.3." should read --from about 5.8 to about 6.3.--

Signed and Sealed this

Fifteenth Day of August, 1989

Attest:

DONALD J. QUIGG

Attesting Officer

Commissioner of Patents and Trademarks